United States Patent [19]
Billeter et al.

[11] Patent Number: 5,046,835
[45] Date of Patent: Sep. 10, 1991

[54] APPARATUS FOR TESTING VISUAL FUNCTIONS OF HUMAN EYES

[75] Inventors: Ernst Billeter, Bergdietikon; Hans Bebie, Oberbottigen, both of Switzerland

[73] Assignee: Interzeag AG, Schlieren, Switzerland

[21] Appl. No.: 410,477

[22] Filed: Sep. 21, 1989

[30] Foreign Application Priority Data

Sep. 22, 1988 [CH] Switzerland .................. 3507/88

[51] Int. Cl.$^5$ .............................................. A61B 3/14
[52] U.S. Cl. .................................... 351/206; 351/224; 351/243
[58] Field of Search ............... 351/211, 222, 224, 239, 351/243, 225, 226, 206, 62

[56] References Cited

U.S. PATENT DOCUMENTS

| | | | |
|---|---|---|---|
| 3,536,383 | 10/1970 | Cornsweet et al. | 351/211 |
| 3,718,386 | 2/1973 | Lynn et al. | |
| 4,021,128 | 3/1977 | Regan. | |
| 4,265,534 | 5/1981 | Remijan | 356/2 |
| 4,376,573 | 3/1983 | Matsumura et al. | 351/211 |

FOREIGN PATENT DOCUMENTS 2843287 10/1978 Fed. Rep. of Germany.
2096791 3/1982 United Kingdom.

*Primary Examiner*—Rodney B. Bovernick
*Assistant Examiner*—J. P. Ryan
*Attorney, Agent, or Firm*—Peter K. Kontler

[57] ABSTRACT

An automatic perimeter wherein the eye to be examined is maintained in a predetermined position to look at an eyepiece which focuses enlarged images of a series of stimuli on the retina. Stimuli are presented by a light emitting diode in combination with a diaphragm and are projected into selected locations around the optical axis of the eye. The perimeter operates without a cupola and is further provided with a system for illuminating the area in front of the eye as well as with a camera which images the eye onto the screen of a monitor so that the person in charge can ascertain whether or not the eye is focused upon a reference point on the optical axis of the eyepiece.

18 Claims, 4 Drawing Sheets

APPARATUS FOR TESTING VISUAL FUNCTIONS OF HUMAN EYES

BACKGROUND OF THE INVENTION

The invention relates to improvements in apparatus for testing visual functions of human eyes, and more particularly to improvements in apparatus which employ so-called perimeters.

The testing of visual functions embraces perimetry, determination of sharpness of visual perception on the retina, determination of flicker frequency, determination of contrast sensitivity and color contrast sensitivity and many others. Apparatus which can carry out such tests are called automatic perimeters and are available for many years. As a rule, the eye to be examined is moved to a position at or close to the center of a hollow hemisphere known as cupola. The eye which is moved to such position is supposed to be directed toward the apex of the cupola, and more particularly toward the apex of the hemispherical internal surface of the cupola. A projector is employed to present stimuli at selected points of the internal surface of the cupola, and the patient or subject is supposed to generate signals in response to detection or non-detection of stimuli.

A drawback of presently known perimeters is that they are bulky and expensive. As a rule, the diameter of a cupola is in the range of 60-100 cm. The center of the cupola is normally located at the eye level of a subject who is seated during examination. Therefore, the overall height of an automatic perimeter is necessarily in the range of two meters. This is the reason that automatic perimeters are normally found only in hospitals and in establishments (employing or owned by ophthalmologists) which specialize in the detection and treatment of diseases and defects of human eyes. Such rather bulky and highly expensive automatic perimeters are much less likely to be found in the offices of individual eye doctors or opticians who are not likely to invest substantial sums of money and whose offices are not likely to have the required space for an instrument which might not be used as frequently as in a highly specialized establishment.

OBJECTS OF THE INVENTION

An object of the invention is to provide an apparatus for testing visual functions of human eyes which is just as versatile and just as accurate as heretofore known apparatus but occupies only a fraction of the space which is taken up by a conventional automatic perimeter.

Another object of the invention is to provide an automatic perimeter which need not be equipped with a cupola.

A further object of the invention is to provide an apparatus which is not only more compact but is also much less expensive than a standard automatic perimeter.

An additional object of the invention is to provide the apparatus with novel and improved means for presenting stimuli to the eye of a subject in the course of a perimetric examination.

A further object of the invention is to provide a novel method of enhancing the compactness of an automatic perimeter without affecting the quality of examination.

Still another object of the invention is to provide an apparatus which renders it possible to constantly monitor the eye in the course of a perimetric examination.

A further object of the invention is to provide the apparatus with novel and improved means for presenting and influencing stimuli.

An additional object of the invention is to provide an apparatus which enables a patient to move her or his eye in the course of a perimetric examination without affecting the results of the test.

SUMMARY OF THE INVENTION

One feature of the invention resides in the provision of an apparatus for testing visual functions of a human eye which is maintained in or close to a predetermined position while its optical axis assumes a predetermined orientation. The apparatus comprises a light emitting diode or another suitable source of radiation (e.g., a halogen lamp or a laser) including means for directing radiation toward the position of the eye, a diaphragm or other suitable means for presenting to the eye in predetermined position a sequence of stimuli at selected intervals and at selected locations in the region of the optical axis, and optical means interposed between the source and the predetermined position for the eye and including means for producing sharp images of stimuli on the retina of the eye in the predetermined position. The presenting means is or can be designed to present stimuli in or close to a single predetermined plane. The presenting means can form part of the aforementioned optical means. As mentioned above, the presenting means can include a diaphragm which is designed to intercept some radiation from the source and has an aperture which imparts to non-intercepted radiation a predetermined size and shape; such non-intercepted radiation constitutes a stimulus.

The means for producing sharp images can include an eyepiece having at least one lens which enlarges the images of stimuli on the retina of the eye in the predetermined position. The presenting means of such apparatus is operative to present stimuli in or close to a predetermined plane; the optical means of such apparatus preferably further comprises means for producing real intermediate images of stimuli between the predetermined pane and the eyepiece. The means for producing real images can comprise means for projecting such images into a second plane, and the eyepiece is then focused upon the second plane. If the radiation source is designed to emit a cone of divergent radiation, the apex angle of such cone is preferably less than 21°.

The apparatus further comprises means for at least substantially uniformly illuminating the area around the optical axis of the eye in predetermined position, and such illuminating means can comprise a source of light and means for influencing at least one parameter of light in a different way for each stimulus. The at least one parameter can constitute the timing of emission of light from the respective source, the amplitude of light or the wavelength of light. Such apparatus can further comprise means for selecting the density profile of the stimuli, e.g., by selecting the density profile of light which is emitted by the respective source.

The apparatus can comprise means (such as a computer) for influencing the radiation source (such as the aforementioned light emitting diode or diodes) to select the amplitude of stimuli as a function of time.

Still further, the apparatus can comprise a drive which serves as a means for jointly moving the radiation source, the stimuli presenting means and the means for producing real images of stimuli in one or more directions substantially at right angles to the optical axis of the eyepiece (such axis preferably coincides with or is parallel to the optical axis of the eye in the predetermined position).

The apparatus can comprise means for supporting one or more lenses or other correcting elements for spherical and/or cylindrical defects of the eye in the predetermined position. Such supporting means can be installed between the eyepiece and the predetermined position for the eye to be examined.

The eyepiece can include means for converting divergent radiation from the means for producing real images of stimuli into a bundle of parallel rays. One or more lenses of the eyepiece are or can be adjustable in the direction of the optical axis of the eyepiece to compensate for certain defects of the eye in the predetermined position.

The apparatus can comprise a source of coherent radiation and a partly transmitting first mirror which extends across the optical axis of the eyepiece and is located in the path of propagation of coherent radiation to establish on the optical axis of the eyepiece a fixation mark for the eye in the predetermined position. The source of coherent radiation can include or is combined with one or more optical elements ahead of the mirror, and a second partially transmitting mirror can be placed across the optical axis of the optical element or elements in the path of propagation of coherent radiation toward the first mirror to transmit visible light but to deflect infrared light into a video camera, particularly into a CCD camera. Means can be provided to direct infrared light upon the eye in the predetermined position.

A diffusor can be placed between the source of light which serves to illuminate the area around the optical axis of the eye in the predetermined position and the respective partly reflecting mirror. Furthermore, a collector lens can be installed between the diffusor and the associated mirror.

A radiation deflecting mirror can be placed between the radiation source and the means for producing real images to allow for a reduction of overall dimensions of the apparatus. One or more additional mirrors can be used to enhance the compactness of the apparatus, e.g., an additional mirror can be placed between the aforementioned diffusor and the associated partly transmitting mirror.

A screen can be placed into the plane in which stimuli are presented to facilitate the displaying of stimuli.

The means for producing sharp images can include a field lens which directs parallel rays along a path toward the eye in the predetermined position, and a collector lens which focuses the rays upon the lens of the eye in the predetermined position. A further diaphragm can be placed into the path of propagation of parallel rays, and such diaphragm is preferably movable in at least one direction transversely of the path of parallel rays. For example, the further diaphragm can be moved in two directions at right angles to each other. The diaphragm of the stimuli presenting means is disposed between the radiation source and the means for directing parallel rays, and the optical element of such directing means is focused upon the aperture of the diaphragm of the stimuli presenting means. A further optical element can be provided to focus radiation from the radiation source upon the aperture of the diaphragm of the stimuli presenting means.

The just described modified apparatus also comprises means for illuminating the area around the optical axis of the eye in the predetermined position, and such illuminating means can include a source of diffused light and a deflecting mirror disposed between the further diaphragm and the focusing means to direct diffused light toward the focusing means. Still further, the modified apparatus can comprise a partially transmitting mirror which is installed between the deflecting mirror and the source of diffused light to transmit visible light but to deflect infrared light into a camera which images the eye upon the screen of a mirror. A fixation mark can be produced for the eye in the predetermined position by resorting to a partially transmitting mirror between the source of diffused light and the aforementioned deflecting mirror.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain presently preferred specific embodiments with reference to the accompanying drawing.

DESCRIPTION OF PREFERRED EMBODIMENTS

Figure 1:
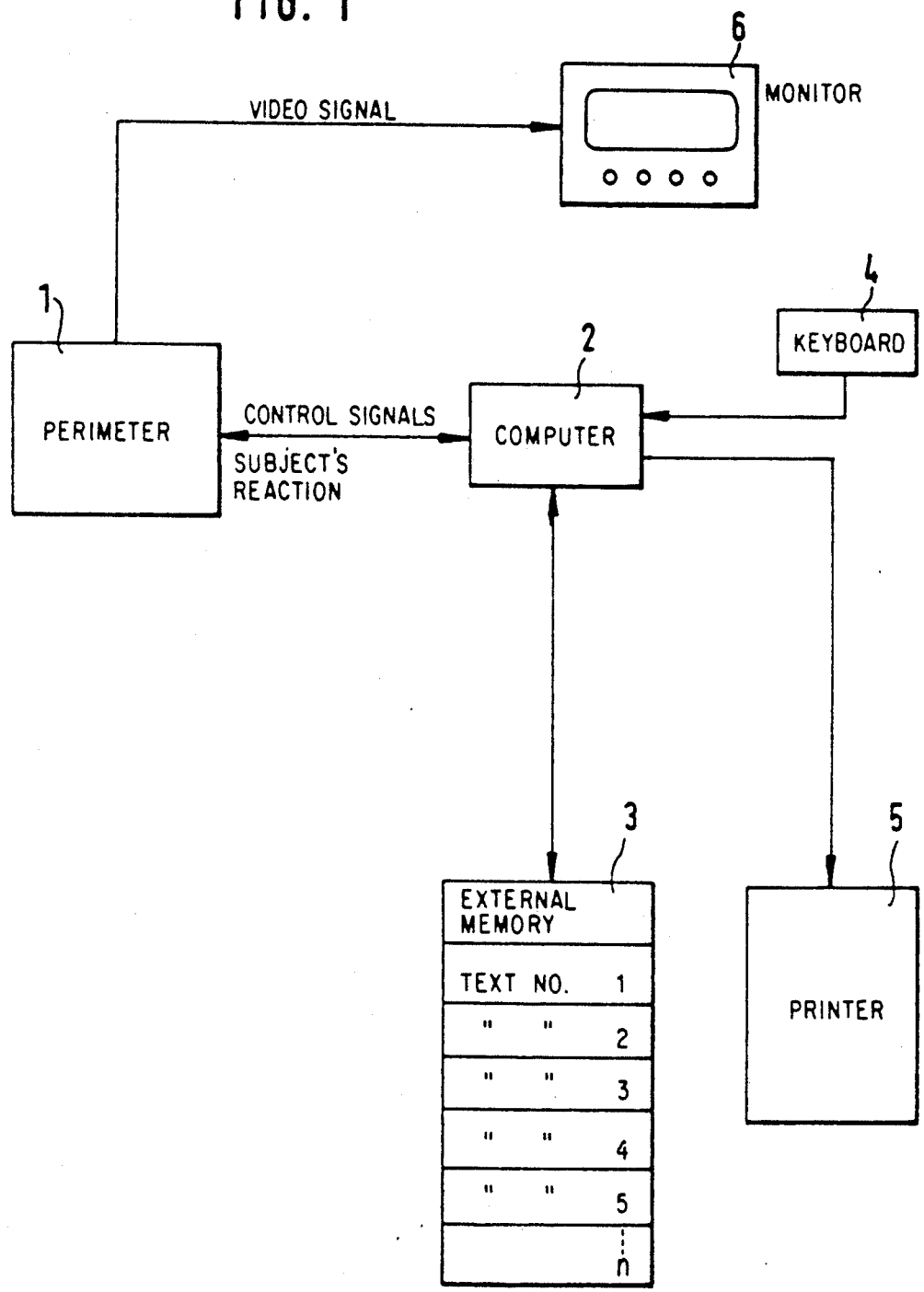
FIG. 1 is a diagrammatic view of an automatic perimeter which embodies the invention.

FIG. 1 shows an apparatus which constitutes an automatic perimeter and embodies one form of the present invention. The actual perimeter of this apparatus comprises means of conventional design for positioning the eye 10 (FIG. 2) of a patient or subject in a predetermined position for testing visual functions of the properly positioned eye. The eye 10 in the position of FIG. 2 receives suitable stimuli at timely spaced intervals from a radiation source 13 (FIG. 2) by way of a stimuli presenting means 14 in the form of a diaphragm between the radiation source 13 and the eye 10. The reference character 9 denotes the optical axis of the lens of the eye 10, and such eye is positioned to see in a predetermined direction, namely the optical axis 9 is oriented to enable the eye to face toward radiation which passes through the aperture of the diaphragm (stimuli presenting means) 14. Stimuli are presented to the eye 10 in the area surrounding the optical axis 9 in front of the properly positioned eye.

The operation of the perimeter 1 is controlled by a computer 2 which comprises a suitable internal memory (not specifically shown) and is or can be operatively connected with an external memory 3 for storage of information pertaining to first, second, third ... n-th examinations of a particular eye 10. The input or inputs of the computer 2 are connected with a source of control signals here shown as a keyboard 4. The information which is stored in the internal memory of the computer 2 and/or in the external memory 3 can include the ascertained threshold values of local light-discriminating sensitivity of the examined eye 10. Reference may be had to commonly owned U.S. Pat. Nos. 4,334,738 and 4,334,739 granted to Erich Seckinger on June 15, 1982.

The apparatus of FIG. 1 further comprises a printer 5 which constitutes a source of recorded numerical and/or graphical information pertaining to data which are stored in the internal memory of the computer 2 and/or in the external memory 3. Furthermore, the apparatus comprises a monitor 6 which has a screen serving as a means for facilitating observation of the eye 10 during examination, for example, in order to ascertain whether or not the eye 10 is focused upon a selected mark so that stimuli are presented at predetermined locations with reference to the optical axis 9. In addition, the monitor 6 is operatively connected with the computer 2.

Figure 2:
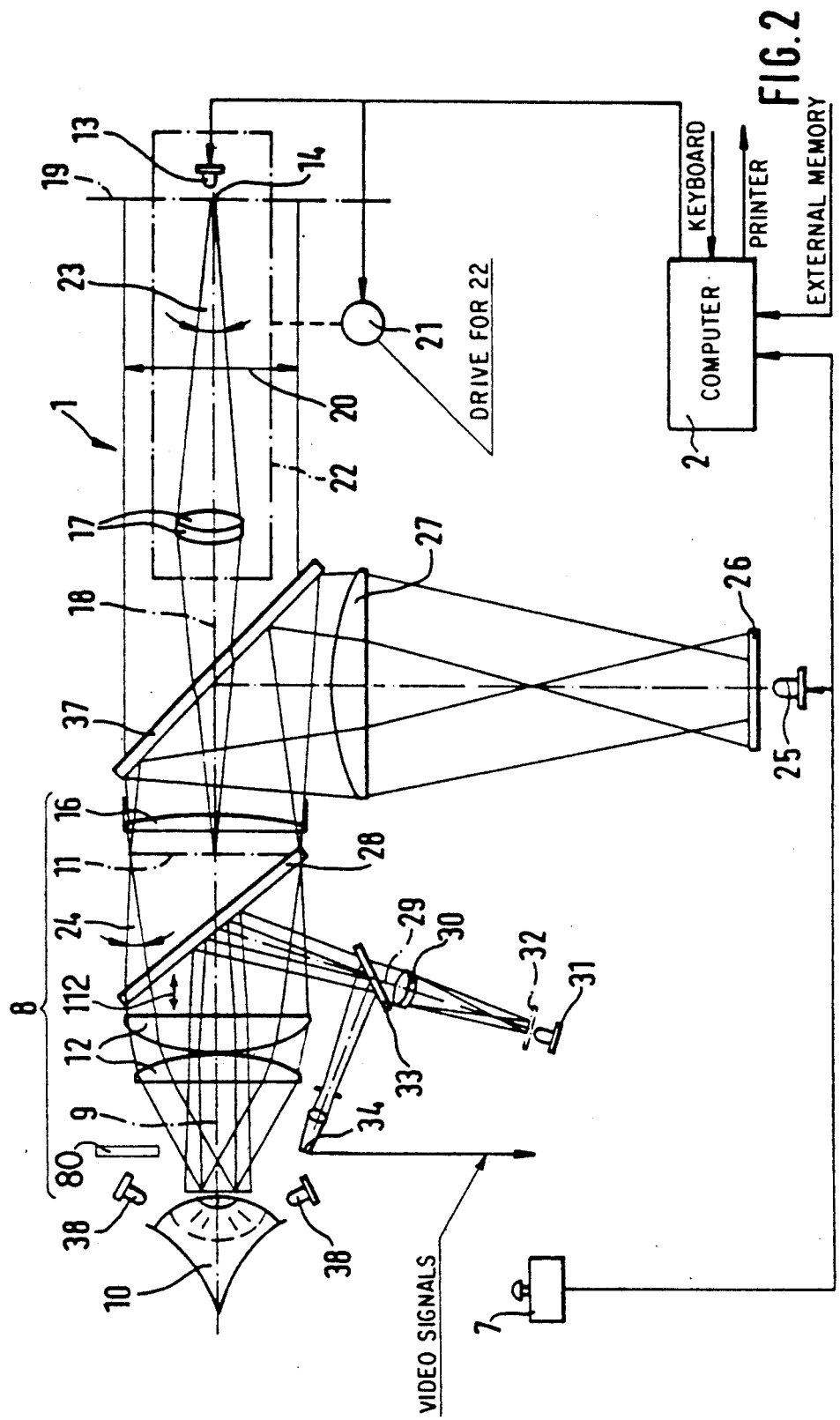
FIG. 2 is a more detailed diagrammatic view of the apparatus of FIG. 1.

While the perimeter 1 is in the process of examining or testing an eye 10 in the predetermined position of FIG. 2, the subject can depress a knob 7 forming part of a means for transmitting signals from the subject to the corresponding input of the computer 2 as well as to one or more components of the perimeter 1. The subject (patient) can depress the knob 7 to transmit to the computer 2 a signal whenever the eye 10 occupying the position of FIG. 2 has perceived a stimulus. Alternatively, the subject will be instructed to depress the knob 7 when she or he fails to perceive a stimulus at a time a stimulus is being presented by the diaphragm 14.

The perimeter 1 of FIG. 2 further comprises an optical system which includes the aforementioned stimuli presenting diaphragm 14, an eyepiece 8 with one or more optical elements 12 between the diaphragm 14 and the eye 10, and a collector lens system 17 constituting a means for producing real intermediate images of stimuli from the diaphragm 14 in a plane 11 between the plane 19 of the aperture of the diaphragm 14 and the optical element or elements 12 of the eyepiece 8. The purpose of the eyepiece 8 is to provide sharp images of stimuli in the plane 11 upon the retina of the eye 10 in the predetermined position of FIG. 2. The optical axis of the optical element or elements 12 (FIG. 2 shows two optical elements 12) of the eyepiece 8 coincides with or is parallel to the optical axis 9 of the lens of the axis of the eye 10 if the eye is properly oriented with reference to the components of the perimeter 1.

The plane 11 of the real images of stimuli can be flat or slightly curved. The optical elements 12 are focussed upon the plane 11 and are ground in such a way that they convert divergent beams of radiation which propagates itself beyond a selected point in the plane 11 into parallel rays and direct the parallel rays toward the eye 10 in the position of FIG. 2. It can be said that, with reference to the plane 11 of the real images of stimuli, the eyepiece 8 constitutes a magnifying lens system.

An advantage of optical elements 12 (which direct parallel rays toward the eye 10 in the position of FIG. 2) is that the eye can be moved, within certain limits, transversely of the optical axis 9 without affecting the sharpness of stimuli and/or without preventing the subject from perceiving those stimuli which would have been perceived by an eye occupying the prescribed or optimum position of FIG. 2. Furthermore, the eye 10 can be shifted at right angles to the optical axis 9 without causing improper perception by the subject of the geometrical position of presented stimuli.

The radiation source 13 is controlled by the computer 2 and can comprise one or more light emitting diodes. An advantage of a radiation source (13) which comprises one or more light emitting diodes is that the emission of radiation toward the aperture of the diaphragm 14 can be regulated without delay. Moreover, a standard light emitting diode can be readily replaced with a diode for emission of colored light if the improved apparatus comprises means for carrying out color perimetric examinations. However, it is equally within the purview of the invention to provide a radiation source 13 which employs one or more halogen lamps or a source of laser beams.

The aperture of the diaphragm 14 determines the size and the shape of stimuli which are transmitted toward the collector lens 17, i.e., toward the means for transmitting real images of stimuli into the plane 11. The aperture of the diaphragm 14 transmits a beam of coherent light, and this diaphragm is located in the focal plane 19 of the collector lens 17. The optical axis 18 of the collector lens 17 coincides with or is parallel with the optical axis 9 of the eye 10 and eyepiece 8. This collector lens can comprise one or more optical elements. The eyepiece 8 enlarges the real image of a stimulus in the plane 11 and transmits such image into a selected part of the area around or on the optical axis in front of the eye 10.

The collector lens 17, the diaphragm 14 and the radiation source 13 constitute an assembly 22 (denoted by a phantom-line square) which is movable at right angles to the optical axis 9 by a computer-controlled drive 21. This enables the diaphragm 14 to move its aperture in the plane 19 at right angles to the optical axes 9 and 18 in order to ensure that stimuli will be presented at any desired point of the plane 19 within the area 20 surrounding the assembly 21 and being within the range of movability of this assembly under the action of the drive means 21. The coordinates of locations of successively presented stimuli in the area 20 will be selected by the computer 2 in accordance with a predetermined program.

The angle 23 denotes the apex angle of the cone of radiation which issues from the aperture of the diaphragm 14. Such angle is preferably less than 20°. The magnitude of the angle 23 depends upon the diameter of the collector lens 17, and such diameter can be selected from a wide range of diameters, the same as the distance of the lens 17 from the plane 19 of the diaphragm 14. The angle 23 preferably matches or at least approximates the angle 24 of divergence of two beams of radiation which issue from a selected point of the plane 11 and propagate themselves toward the nearest optical element 12 of the eyepiece 8. The magnitude of the angle 23 or 24 determines the deviation tolerance of a subject's eye 10 in the position of FIG. 2.

In order to uniformly illuminate the entire observable area or field around the optical axis 9 in front of the eye 10 in the position of FIG. 2, the perimeter 1 further comprises a partially transmitting mirror 37 which crosses the optical axes 9 and 18 between the collector lens 17 and the eyepiece 8 to direct light from a light source 25 receiving signals from the knob 7, i.e., from the subject who manipulates the knob 7. The mirror 37 directs light issuing from the source 25 toward the eye 10. At the same time, the mirror 37 permits radiation to pass from the collector lens 17 toward the eyepiece 8. Uniformity of illumination of the area around the optical axis 9 is enhanced if the perimeter 1 further comprises a disc-shaped or otherwise configurated diffusor 26 which is installed between the light source 25 and the mirror 37. A collector lens 27 (e.g., a Fresnel lens) can be installed between the diffusor 26 and the mirror 37.

The diffusor 26 can serve as a color filter if the apparatus of the present invention is used for color perimetry.

The perimeter 1 further comprises means for providing to the eye 10 in the position of FIG. 1 a reference point or fixation mark. This is likely to more reliably ensure that the optical axis 9 of the eye 10 will coincide with or will remain parallel to the optical axis of the eyepiece 8 in the course of an examination. For example, the reference point or fixation mark can constitute a bright spot upon which the eye 10 is fixed in the course of a perimetric test. To this end, a partially transmitting mirror 28 is placed between the plane 11 and the optical elements 12 of the eyepiece 8 to permit radiation to pass from the plane 11 toward the eye as well as to present a bright spot in the form of light which is emitted by a further light source 31 and passes through the aperture of a diaphragm 32 on its way toward an optical element 30 (e.g., two lenses) which projects the light spot upon the mirror 28 for observation by the eye 10. The aperture of the diaphragm 32 determines the size and shape of the spot or mark on the mirror 28.

The optical axis 29 of the element 30 is crossed by a further partially transmitting mirror 33 which transmits visible light from the source 31 but reflects infrared light from the eye. Deflected infrared light is directed toward an infrared light-sensitive CCD camera 34 serving to permit observation of the optical axis 9 and of the eye 10 in the course of an examination. The camera 34 transmits images to the screen of the monitor 6, and this enables the physician in charge of carrying out the test to ascertain whether or not the eye 10 is actually directed toward the bright spot on the mirror 28. Two or more light sources 38 are or can constitute or include diodes which emit infrared light to thus permit "secret" visual observation of the eye 10 in the course of a perimetric examination.

In accordance with a modification which is not shown in the drawing, the collector lens 17 and a field lens 16 adjacent the plane 11 can be omitted if the radiation source 13 and the diaphragm 14 are moved so close to the eyepiece 8 that the plane 19 of the diaphragm 14 coincides with the plane 11 of real images of stimuli provided by the diaphragm 14. This can be realized by placing a screen into the plane 11. If such screen is provided in the plane 11 to present stimuli to the eye 10 in the position of FIG. 2, it is possible to select the stimuli in such a way that they are darker than the surroundings.

In either of the above described embodiments, the distance of the eye 10 from the plane 11 of real images of stimuli is shorter than the sharp visual range or distance.

An advantage of the improved apparatus is that the perimeter 1 can operate without a cupola, i.e., without the bulkiest component of a conventional perimeter. The stimuli presenting means in the form of a simple diaphragm (14) also contributes to compactness and lower cost of the improved apparatus. Moreover, and since the eyepiece 8 acts not unlike a magnifying glass, the stimuli presenting and other means can be miniaturized to even further enhance the compactness of the apparatus.

The collector lens 17 renders it possible to provide real images of stimuli in a plane (11) in immediate or close proximity to the eyepiece 8. In addition, the collector lens 17 renders it possible to provide simple but effective means (including the light source 25) for uniformly illuminating the area around the optical axis 9 as well as to provide simple and compact means (including the radiation source 31) for providing a fixation mark for the eye 10 in the position of FIG. 2. The intensity of radiation which is supplied by the source 25 can be regulated in any known manner to select the brightness of the area around the optical axis 9. As mentioned above, the diffusor 26 can serve as a color filter if the structure of FIG. 2 is used for color perimetry. The density profile of radiation which passes through the diaphragm 14 can be regulated by the computer 2 via radiation source 13. The computer 2 can also serve to regulate the density profile of radiation which is emitted by the source 25.

The provision of drive 21 and of the aforementioned assembly 22 including the radiation source 13, diaphragm 14 and collector lens 17 renders it possible to present to the retina of the eye 10 a sharply defined image of a stimulus at any selected point in the field of view of the eye assuming the position of FIG. 2.

The combination of eyepiece 8 and collector lens 17 exhibits the advantage that the eye 10 can leave the position of FIG. 2 by moving (within limits) transversely of the optical axis of the eyepiece 8 without affecting the detectability and/or the geometric positions (coordinates) of stimuli. Such freedom of movement of the eye transversely of the optical axis of the eyepiece 8 reduces the likelihood of excessive and premature tiredness of the eye in the course of a perimetric examination with the apparatus of FIG. 2. It has been found that the just discussed freedom of movement of the eye at right angles to the optical axis 9 enables a patient to more readily endure a complete perimetric examination than if the eye were required to remain in one and the same position in the course of a complete examination.

At least one optical element 12 of the eyepiece 8 is preferably adjustable in the direction of the optical axis 9 (note the arrow 112). This renders it possible to compensate for spherical defects of the eye.

The provision of a fixation mark or reference or observation point for the eye of a patient or subject undergoing perimetric examination is known in the art. However, the illustrated means 28, 30, 31, 32 for providing a fixation mark exhibits the advantage that it does not necessitate the provision of a hole in the field of view and the provision of means for eliminating the problems which arise in a conventional perimeter as a result of the need for such hole.

An advantage of the sources 38 of infrared light is that the camera 34 can observe the eye 10 during each stage of a perimetric examination and that such observation does not cause irritation to the eye and/or any other problems to the patient or subject. The eye can be displayed on the screen of the monitor 6 so that the person in charge can readily ascertain whether or not the subject or the patient should be instructed to look at the fixation mark.

A support 80 for temporary reception of correcting lenses or analogous parts (to compensate for cylindrical and/or spherical defects of the eye 10 in the position of FIG. 2) is provided between such position for the eye and the eyepiece 8.

The computer 2 can influence, for each stimulus, at least one parameter (such as the timing of emission, the amplitude and/or the wavelength) of light which issues from the source 25.

Furthermore, the computer 2 can serve as a means for selecting the density profile of stimuli and/or of light from the source 25.

Figure 3:
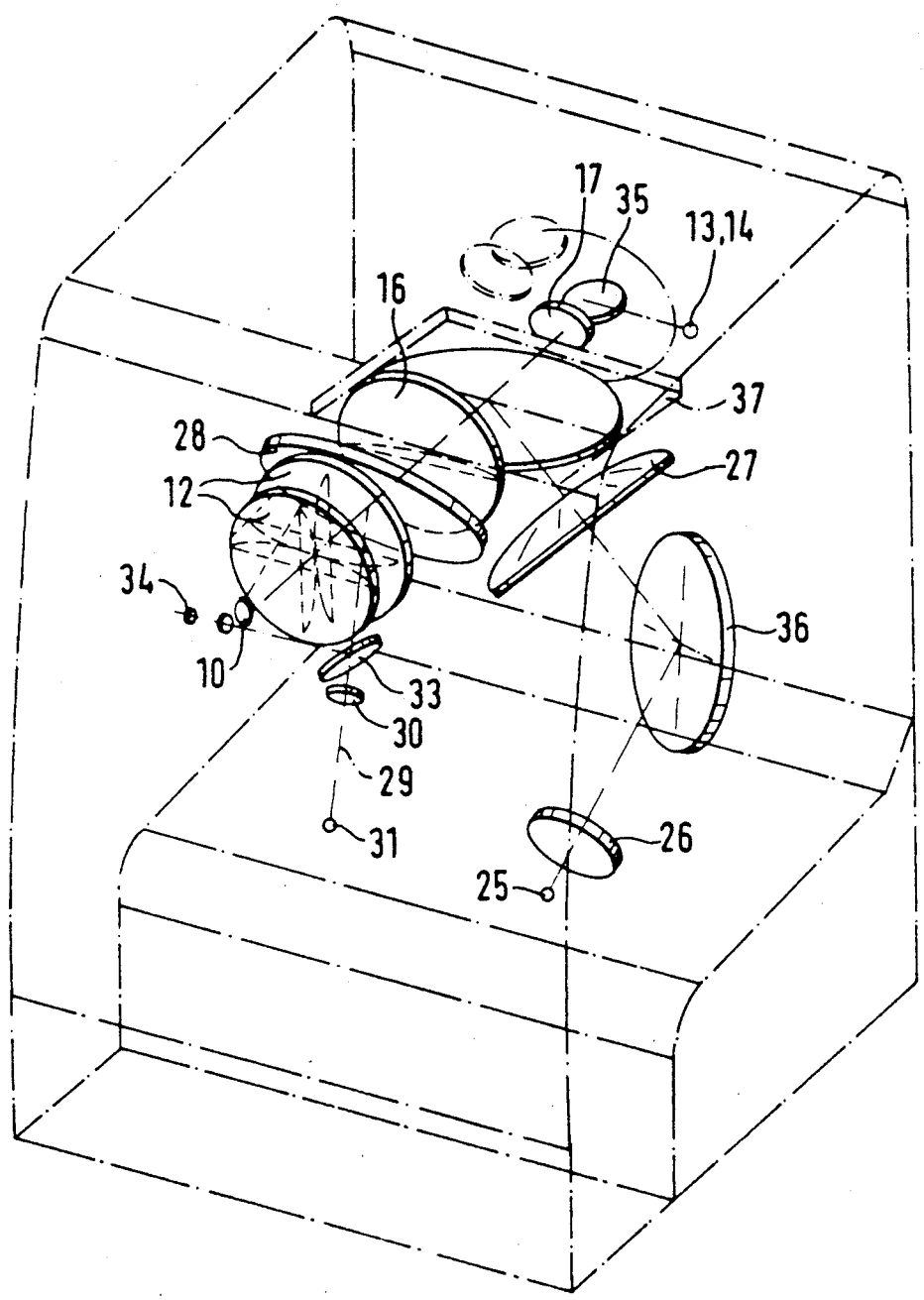
FIG. 3 is a perspective view of an apparatus of the type shown in FIG. 2.

FIG. 3 illustrates a more compact version of the perimeter 1 of FIG. 2. This modified perimeter comprises an additional radiation deflecting mirror 35 between the diaphragm 14 and radiation source 13 on the one hand, and the collector lens 17 on the other hand. A further radiation deflecting mirror 36 is positioned between the diffusor 26 and the collector lens 27 of the means for uniformly illuminating the area around the optical axis 9 of the eye 10 in the region of the optical elements 12 of the eyepiece. The provision of mirrors 35 and 36 renders it possible to confine the components of the perimeter and the screen in a relatively small housing or casing (shown in FIG. 3). The compactness of the structure which is shown in FIG. 3 can be enhanced still further by resorting to one or more additional radiation deflecting mirrors or the like.

Figure 4:
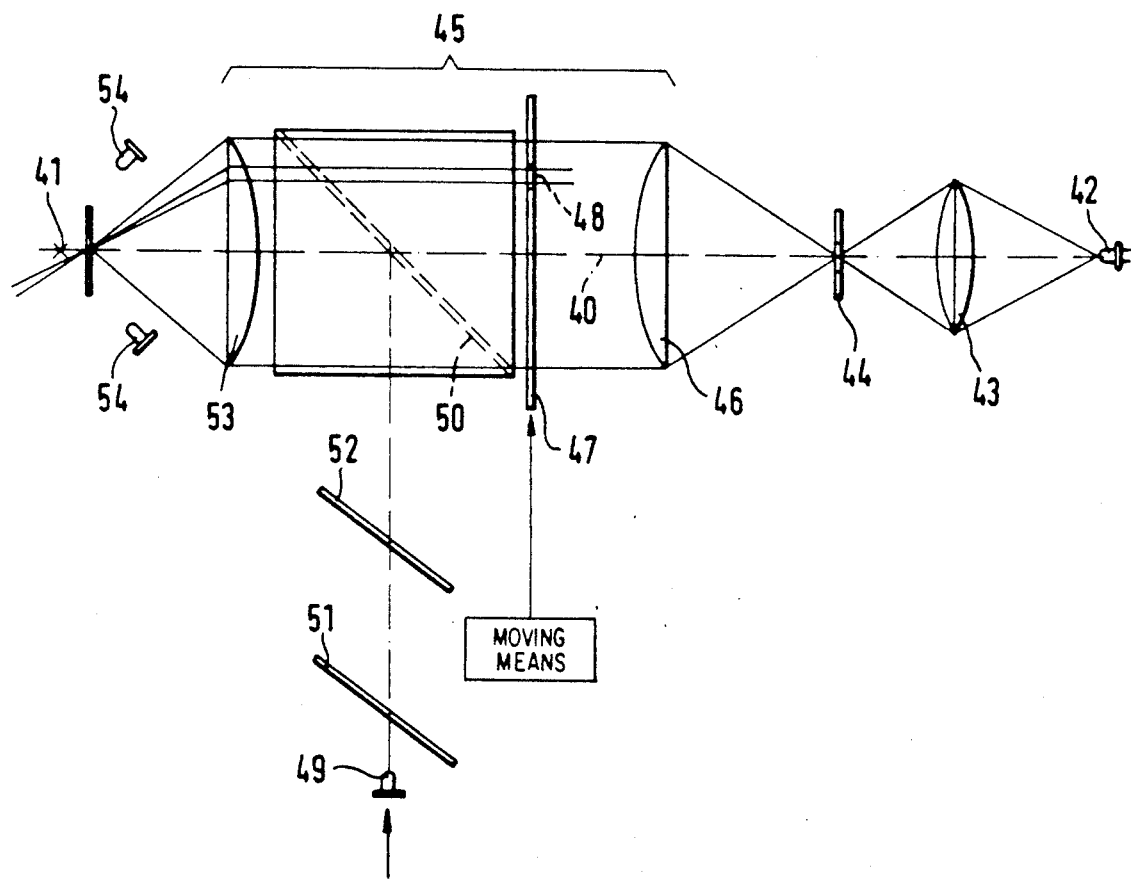
FIG. 4 is a diagrammatic view of a modified apparatus.

FIG. 4 shows a further embodiment of the improved cupola-less perimeter. The method of assembling this perimeter is based on the so-called Maxwellian view, namely a method of using an optical instrument in which a real image of a radiation source is focused upon the pupil of the eye in lieu of resorting to an eyepiece. The predetermined position of the eye to be examined is shown at 41 and is located on the optical axis 40 of the optical system of this perimeter. A radiation source 42 directs radiation toward a condenser lens 43 which focuses such radiation upon the aperture of a diaphragm 44 serving to present stimuli to a field lens 46. The latter directs parallel rays along a path 45 toward a collector lens 53 which, in turn, focuses radiation upon the center of the pupil of the eye in the position 41. This ensures that defects of the eye cannot influence the presentation of stimuli to the retina.

The perimeter of FIG. 4 further comprises a further diaphragm 47 which extends across the entire path 45 of parallel rays between the lenses 46 and 53 and has an aperture 48 which is movable transversely of the optical axis 40 in a plurality of directions, for example, in as well as at right angles to the plane of FIG. 4. This enables the further diaphragm 47 to move its aperture 48 into any selected portion of the path 45 of parallel rays. The aperture 48 determines the size and shape of stimuli. The means 147 for moving the further diaphragm 47 transversely of the path 4 in at least two directions receives signals from the computer 2 (not shown in FIG. 4). Such arrangement enables the computer to select the coordinates of stimuli which are focussed by the lens 53 upon the center of the pupil of an eye occupying the position 41.

The means for uniformly illuminating the area around the optical axis 40 includes a source 49 of diffused light and a partially transmitting mirror 50 which crosses the optical axis 40 in the path 45 of parallel rays to direct light from the source 49 toward the collector lens 53.

A further partially transmitting mirror 51 constitutes one element of the means for presenting to the eye at the position 41 a bright spot to serve as a fixation mark or observation point in the course of a perimetric examination. The remaining parts of the means for presenting a fixation mark can be identical with those shown at 30 and 31 in FIG. 2.

An additional partially transmitting mirror 52 corresponds to the mirror 33 of FIG. 2 and serves to transmit visible light toward the optical axis 40 but to deflect infrared light toward a camera corresponding to the CCD camera 34 of FIG. 2.

Two infrared light emitting diodes 54 are provided to "secretly" illuminate the eye at the position 41 for observation on the screen of the monitor 6, not shown in FIG. 4.

The optical elements of perimeters which are shown in FIGS. 2, 3 and 4 can comprise individual lenses or groups of two or more lenses each. For the sake of clarity and simplicity, the perimeters of FIGS. 2 to 4 are shown as embodying primarily optical elements each of which comprises a single lens or a minimal number of lenses.

The perimeter of FIG. 4 exhibits the advantage that the defects of the eye which is being examined do not influence, or do hot appreciably influence, the results of the test. On the other hand, the eye in the position 41 has little or practically no freedom of movement in directions at right angles to the optical axis 40, i.e., even minor movements of the eye at right angles to the axis 40 could adversely effect the results of examination.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. Apparatus for testing visual functions of a human eye which is located in or close to a predetermined position while its optical axis is maintained in a predetermined orientation, comprising a first source of radiation including means for directing radiation toward said position; means for presenting to the eye in said position a sequence of stimuli at selected intervals and at selected locations in the region of the optical axis of the eye; and optical means interposed between said source and said position and including means for producing sharp images of stimuli on the retina of the eye in said position, said presenting means forming part of said optical means and said means for producing sharp images including an eyepiece which is focused upon a predetermined plane, said predetermined position being spaced apart from said predetermined plane by a distance which is shorter than the sharp visual distance; a second source of radiation; and a partially transmitting mirror extending across the optical axis of said eyepiece and located in the path of propagation of radiation from the second source to establish on the optical axis of said eyepiece a mark for the eye in said position.

2. The apparatus of claim 1, further comprising an optical element in the path of propagation of coherent radiation toward said mirror.

3. Apparatus for testing visual functions of a human eye which is located in or close to a predetermined position while its optical axis is maintained in a predetermined orientation, comprising a source of radiation including means for directing radiation toward said position; means for presenting to the eye in said position a sequence of stimuli at selected intervals and at selected locations in the region of the optical axis of the eye; optical means interposed between said source and said position and including means for producing sharp images of stimuli on the retina of the eye in said position, said presenting means forming part of said optical means; and means for at least substantially uniformly illuminating the area around the optical axis of the eye in said position, including a source of light and means for varying at least one parameter of several parameters of light in a different way for each of said stimuli, said parameters including the timing of emission of light from the perspective source, the amplitude of light and the spectrum of light, said at least one parameter being the spectrum of light.

4. Apparatus for testing visual functions of a human eye which is located at or close to a predetermined position while its optical axis is maintained in a predetermined orientation, comprising a source of radiation including means for directing radiation toward said position; means for presenting to the eye in said position a sequence of stimuli at selected intervals and at selected locations in the region of the optical axis of the eye; optical means interposed between said source and said position and including means for producing sharp images of stimuli on the retina of the eye in said position, said presenting means forming part of said optical means; and means for selecting the density profile of said stimuli.

5. Apparatus for testing visual functions of a human eye which is located at or close to a predetermined position while its optical axis is maintained in a predetermined orientation, comprising a source of radiation including means for directing radiation toward said position; means for presenting to the eye in said position a sequence of stimuli at selected intervals and at selected locations in the region of the optical axis of the eye; optical means interposed between said source and said position and including means for producing sharp images of stimuli on the retina of the eye in said position, said presenting means forming part of said optical means; and means for varying said radiation source to vary the amplitude of said stimuli as a function of time.

6. Apparatus for testing visual functions of a human eye which is located in or close to a predetermined position while its optical axis is maintained in a predetermined orientation, comprising a source of radiation including means for directing radiation toward said position; means for presenting to the eye in said position a sequence of stimuli at selected intervals and at selected locations in the region of the optical axis of the eye; optical means interposed between said source and said position and including means for producing sharp images of stimuli on the retina of the eye in said position, said presenting means forming part of said optical means, being operative to present stimuli in a first plane and including a diaphragm; means for producing real images of stimuli in a second plane between said first plane and said means for producing sharp images; and means for jointly moving said diaphragm, said radiation source and said means for producing real images in a plurality of directions substantially at right angles to the axis of said eyepiece.

7. Apparatus for testing visual functions of a human eye which is located at or close to a predetermined position while its optical axis is maintained in a predetermined orientation, comprising a source of radiation including means for directing radiation toward said position; means for presenting to the eye in said position a sequence of stimuli at selected intervals and at selected locations in the region of the optical axis of the eye; optical means interposed between said source and said position and including an eyepiece for producing sharp images of stimuli on the retina of the eye in said position, said presenting means forming part of said optical means; and means for supporting correcting elements for spherical and cylindrical defects of the eye in said position, said supporting means being located between said eyepiece and said position.

8. Apparatus for testing visual functions of a human eye which is located in or close to a predetermined position while its optical axis is maintained in a predetermined orientation, comprising a source of radiation including means for directing radiation toward said position; means for presenting to the eye in said position a sequence of stimuli at selected intervals and at selected locations in the region of the optical axis of the eye; optical means interposed between said source and said position and including means for producing sharp images of stimuli on the retina of the eye in said position, said presenting means forming part of said optical means and said optical means including an eyepiece; a source of coherent radiation; a first partially transmitting mirror extending across the optical axis of said eyepiece and located in the path of propagation of coherent radiation from the respective source to establish on the optical axis of said eyepiece a mark for the eye in said position; an optical element in the path of propagation of coherent radiation toward said mirror; a second partially transmitting mirror crossing the optical axis of said optical element between said optical element and said first mirror to transmit visible light and to reflect infrared light; a monitor; and means for imaging the eye in said position on said monitor.

9. The apparatus of claim 8, wherein said imaging means includes a CCD camera.

10. The apparatus of claim 8, further comprising means for directing infrared light upon the eye in said position.

11. Apparatus for testing visual functions of a human eye which is located at or close to a predetermined position while its optical axis is maintained in a predetermined orientation, comprising a source of radiation including means for directing radiation toward said position; means for presenting to the eye in said position a sequence of stimuli at selected intervals and at selected locations in the region of the optical axis of the eye; optical means interposed between said source and said position and including means for producing sharp images of stimuli on the retina of the eye in said position, said presenting means forming part of said optical means; a source of light; means for directing light from said source of light into the area surrounding the optical axis of the eye in said position; a diffusor between said source of light and said light directing means; a collector lens between said diffusor and said light directing means; and a mirror between said lens and said diffusor.

12. Apparatus for testing visual functions of a human eye which is located at or close to a predetermined position while its optical axis is maintained in a predetermined orientation, comprising a source of radiation including means for directing radiation toward said position; mean for presenting to the eye in said position a sequence of stimuli at selected intervals and at selected locations in the region of the optical axis of the eye; optical means interposed between said source and said position and including means for producing sharp images of stimuli on the retina of the eye in said position, said presenting means forming part of said optical mean and said means for producing sharp images including means for directing parallel rays in a direction from said radiation source toward the eye in said position; means for focusing said rays upon the lens of the eye in said position; a diaphragm having an aperture in the path of propagation of said parallel rays, said diaphragm being movable in at least one direction transversely of said path; and means for illuminating the area around the optical axis of the eye in said position, including a source of diffused light and a deflecting mirror disposed between said diaphragm and said focusing means to direct diffused light toward said focusing means.

13. The apparatus of claim 12, further comprising a partially transmitting mirror between said deflecting mirror and said source of diffused light to transmit visible light and to deflect infrared light, and a camera arranged to receive deflected infrared light.

14. The apparatus of claim 13, further comprising a monitor arranged to display images of the eye which are produced by said camera.

15. The apparatus of claim 12, further comprising means for producing a fixation mark for the eye in said position including a partially transmitting mirror between said source of diffused light and said deflecting mirror.

16. Apparatus for testing visual functions of a human eye which is located at or close to a predetermined position while its optical axis is maintained in a predetermined orientation, comprising a source of radiation including means for directing radiation toward said position; means for presenting to the eye in said position a sequence of stimuli at selected intervals and at selected locations in the region of the optical axis of the eye; optical means interposed between said source and said position and including means for producing sharp images of stimuli on the retina of the eye in said position, said presenting means forming part of said optical means; and means for varying said radiation source to vary the spectrum of said stimuli as a function of time.

17. Apparatus for testing visual functions of a human eye which is located in or close to a predetermined position while its optical axis is maintained in a predetermined orientation, comprising a source of radiation including means for directing radiation toward said position; means for presenting to the eye in said position a sequence of stimuli at selected intervals and at selected locations in the region of the optical axis of the eye; optical means interposed between said source and said position and including means for producing sharp images of stimuli on the retina of the eye in said position, said presenting means forming part of said optical means and said means for producing sharp images including an eyepiece which is focused upon a predetermined plane, said predetermined position being spaced apart from said predetermined plane by a distance which is shorter than the sharp visual distance; a source of light; means for directing light from said last named source into the area surrounding the optical axis of the eye in said position; and a diffusor between said light source and said light directing means.

18. Apparatus for testing visual functions of a human eye which is located in or close to a predetermined position while its optical axis is maintained in a predetermined orientation, comprising a source of radiation including means for directing radiation toward said position; means for presenting to the eye in said position a sequence of stimuli at selected intervals and at selected locations in the region of the optical axis of the eye; optical means interposed between said source and said position and including means for producing sharp images of stimuli on the retina of the eye in said position, said presenting means forming part of said optical means; means for at least substantially uniformly illuminating the area around the optical axis of the eye in said position, including a source of light and means for varying at least one parameter of several parameters of light in a different way for each of said stimuli, said parameters including the timing of emission of light from the respective source, the amplitude of light and the wavelength of the light; and means for selecting the density profile of light.

* * * * *